United States Patent [19]

Davis

[11] Patent Number: 5,188,746
[45] Date of Patent: Feb. 23, 1993

[54] ANTIWEAR/ANTIOXIDANT ADDITIVES BASED ON DIMERCAPTO DERIVATIVES OF ACRYLATES AND METHACRYLATES POLYMERS AND AMINE REACTION PRODUCTS THEREOF

[75] Inventor: Robert H. Davis, Pitman, N.J.

[73] Assignee: Mobil Oil Corporation, Fairfax, Va.

[21] Appl. No.: 607,950

[22] Filed: Nov. 1, 1990

[51] Int. Cl.$^5$ ................. C10M 135/36; C07D 285/12
[52] U.S. Cl. .................................... 252/47.5; 548/142
[58] Field of Search ........................ 252/47.5; 548/142

[56] References Cited

U.S. PATENT DOCUMENTS

| | | | |
|---|---|---|---|
| 2,836,564 | 5/1958 | Roberts et al. | 252/47.5 |
| 3,914,241 | 10/1975 | Elliott et al. | 548/142 |
| 4,136,043 | 1/1979 | Davis | 252/47.5 |
| 4,193,882 | 3/1980 | Gemmill, Jr. | 548/142 |
| 4,584,114 | 4/1986 | Gemmill et al. | 252/47.5 |
| 4,661,273 | 4/1987 | Frangatos et al. | 252/47 |
| 4,784,780 | 11/1988 | Farng et al. | 252/32.7 E |
| 5,055,584 | 10/1991 | Karol | 548/142 |

*Primary Examiner*—Jerry Johnson
*Attorney, Agent, or Firm*—Alexander J. McKillop; Malcolm D. Keen; Marina V. Schneller

[57] ABSTRACT

The invention relates to zinc and phosphorus free additives for lubricating compositions which are produced by a free radical reaction between a dimercaptothiadiazole and monomer oligomer or homologue of acrylates or methacrylate, which in minor amounts impart antiwear/extreme pressure and antioxidation properties to the lubricant.

8 Claims, No Drawings

ANTIWEAR/ANTIOXIDANT ADDITIVES BASED ON DIMERCAPTO DERIVATIVES OF ACRYLATES AND METHACRYLATES POLYMERS AND AMINE REACTION PRODUCTS THEREOF

FIELD OF THE INVENTION

The invention relates to zinc free and phosphorus free additives for lubricants which are antiwear agents and antioxidants and are based on free radical reaction products of dimercaptothiadiazole and acrylates or methacrylates which are derivatives containing sulfur and, optionally, nitrogen.

BACKGROUND OF THE INVENTION

Replacement of zinc phosphorodithioates by zinc and phosphorus-free antiwear additives in circulating oils, gear oils and various other lubricating systems is considered highly desirable because of environmental considerations and the potential electrolytic corrosivity of zinc salts. An additive system which in addition to antiwear activity exhibits antioxidant activity and metal, e.g. copper, passivation is highly desirable. The condensates of the present invention provide outstanding FZG gear performance, low Four-ball wear and antioxidant activity. Furthermore, compositions of the invention are substantially free of corrosive elemental sulfur.

SUMMARY OF THE INVENTION

The invention provides antiwear agents possessing antioxidant activity which are phosphorus and zinc free. In addition, the invention provides lubricants containing said antiwear agents which exhibit increased resistance to oxidation and increased wear reduction characteristics.

The antiwear agents possessing antioxidant activity are dimercaptothiadiazole adducts of monomeric, oligomeric, or polymeric methacrylates and acrylates, and include reaction products of said dimercaptothiadiazole adducts with amines.

DETAILED DESCRIPTION OF THE INVENTION

The dimercaptothiadiazole adducts of acrylates and methacrylates, and amine reaction products thereof, provide exceptional antiwear/extreme pressure (EP) and antioxidant activity with potential metal deactivating and viscosity improving properties. The products of the invention provide outstanding FZG gear performance, low Four-ball wear and good antioxidant activity, and, most significantly, are free of both zinc and phosphorus. The beneficial properties of the compositions of the invention derive from chemical structures containing dimercaptothiadiazole derived groups, polymeric or oligomeric methacrylate and/or acrylate groups and amine/amide/amine salt linkages within the same molecule. The products of the invention show good stability and compatibility when used in the presence of other commonly used additives in lubricant compositions.

The dimercaptothiadiazole adducts of acrylates and methacrylates can be represented as an empirical formula [A]:

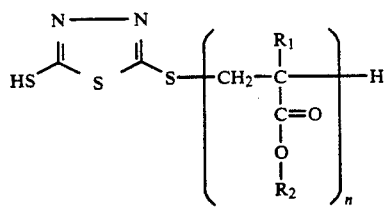

Reaction products of an amine and the dimercapto thiadiazole acrylo derivative, in accordance with the invention, can be designated by an empirical formula [B]:

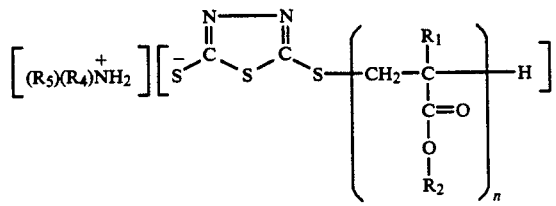

The dimercaptothiadiazole-acrylate derivatives are formed by reacting dimercaptothiadiazole with a monomer or oligomer of an acrylate or an alkylacrylate in the presence of radical initiators (catalysts) known in the art for the free radical polymerization of acrylates and alkylacrylates. These initiators, when subjected to heat, electromagnetic radiation, or chemical reaction, will readily undergo homolytic fission into radicals of greater reactivity than the monomer radical. Typical examples are peroxides, persulfates, and azo compounds, e.g. alpha,alpha-azobisisobutyronitrile.

The products thereby formed are dimercaptothiadiazole-derived polymeric or oligomeric methacrylates and acrylates. These polymeric or oligomeric methacrylates/acrylates are then reacted with various amines to form amine/ amide/amine salt derivatives. The actual reactions are complex.

The 2,5-dimercapto-1,3,4-thiadiazole is believed to act as a chain transfer agent in the radical reaction. Since dimercaptothiadiazole possesses two mercapto groups, it may actively transfer two chains. In addition to the predominant chain transfer to dimercaptothiadiazole other chain transfer modes are possible. These other chain transfer modes may include transfer to monomer, transfer to polymer, and transfer to solvent.

The primary effect of chain transfer is a decrease in the polymer chain length. Another result of the chain transfer is that the dimercaptothiadiazole is incorporated into the oligomer backbone to produce oil soluble products. Furthermore, it is noted that, since the dimercaptothiadiazole possesses two mercapto groups, it may actively transfer two chains to result in a composition having an empirical formula [C]:

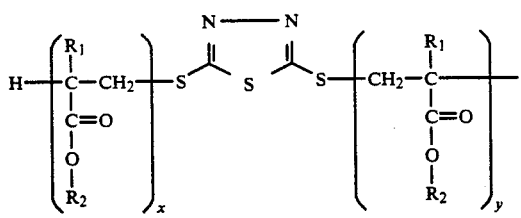

in which, as in [A], [B] and [C] above and [D] below,
$R_1$ is hydrogen or methyl, $R_2$, $R_3$ are hydrogens or a hydrocarbyl of 1 to 30 carbon atoms, x and y is a whole number but $x+y>1$ and n is at least 1, $R_4$ and $R_5$ are hydrogens or hydrocarbon groups of 1 to 60 carbon atoms wherein the hydrocarbon group is selected from the group consisting of alkyl, aralkyl, cycloalkyl, aralkyl or aryl or hydrocarboxyhydrocarbylene groups, and can optionally contain sulfur, nitrogen or oxygen.

When mixtures of alkylacrylates ($M_1$) and acrylates ($M_2$) are employed for reaction empircal formula C would be written as [C⁻] below:

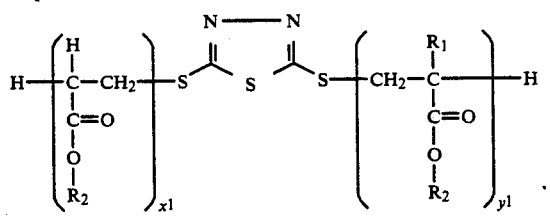

wherein each of $x^1$ and $y^1$ is 0 or a whole number but $x^1+y^1$ is greater than 1,
in which $M_1$ is the

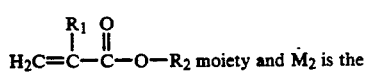

$H_2C=C-C-O-R_2$ moiety and $M_2$ is the

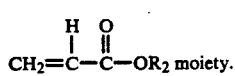

$CH_2=C-C-OR_2$ moiety.

The acrylic esters which can be employed in the invention include the n-alkyl esters, including methyl, ethyl, propyl, butyl, pentyl, hexyl, heptyl, octyl, nonyl, decyl, dodecyl, tetradecyl, and hexadecyl; the secondary and branched-chain alkyl esters, including isopropyl, isobutyl, sec-butyl and 2-ethylhexyl; esters of olefinic alcohols, including allyl, 2-methylallyl and furfuryl; aminoalkylesters, including 2-(dimethylamino)ethyl; 2-(diethylamino) ethyl and 2-(dibutylamino)ethyl; esters of ether alcohols including 2-methoxyethyl and 2-ethoxyethyl and tetrahydrofurfuryl; cycloalkyl esters including cyclohexyl and 4-methylcyclohexyl; esters of halogenated alcohols including 2-bromoethyl, 2-chloroethyl and 2,3-dibromopropyl; and glycol diacrylates including ethylene glycol (monoester); ethylene glycol; propylene glycol, 1,3-propanediol, 1,4-butanediol, diethylene glycol, 1,5-pentanediol, triethylene glycol, dipropylene glycol, 2,5-hexanediol, 2,2-diethyl-1,3-propanediol, 2-ethyl-1,3-hexanediol and 1,10-decanediol. Homopolymers of methacrylate which are conventional include the polymethylmethacrylates, ethyl methacrylates, n-propyl methacrylates, isopropyl methacrylates, n-butyl methacrylates, sec-butyl methacrylates, t-butyl methacrylates, n-hexyl methacrylates, 2-ethylbutyl methacrylates, n-octyl methacrylates, 2-ethyl hexyl metharylates, n-decyl methacrylates, lauryl methacrylates, tetradecyl methacrylates, hexadecyl methacrylates, octadecyl methacrylates, stearyl methacrylates, cyclohexyl methacrylates, isobornyl methacrylates, phenyl methacrylates, benzyl methacrylates, ethylthioethyl methacrylates, 3,3,5-trimethylcyclohexyl methacrylates, and mixtures thereof.

The dimercaptothiadiazole adducts of the acrylates are then optionally reacted with an amine, to produce structures illustrated by an empirical formula [B] above or [D] below.

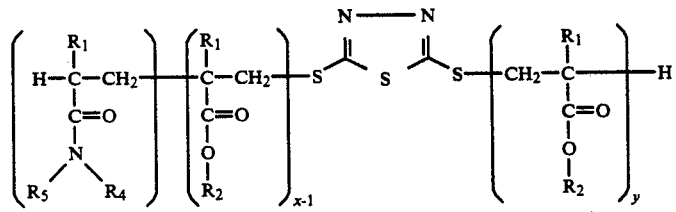

In that formula [D], $R_4$ and $R_5$ are defined as above and x is at least 1. The amine reactant may include polyethylene amine derived polyisobutyl succinimide, ethanol or methanol amine derived polyisobutyl succinimide, ethanol amines, ethoxylated or propoxylated amines, phenylalphanaphthylamines, polymeric amines, or diamines, triamines, or ether amines or other hydrocarbylamines, optionally containing sulfur, oxygen, and/or nitrogen.

The unreacted mercapto groups of the acrylate and/or methacrylate derivatives of dimercaptothiadiazole can react with the amine to produce amine salt derivatives. The ester groups of the methacrylates/acrylates may also react with amines to form amides. Additional reactions are possible, and accordingly, the compositions of the invention may be mixtures.

In accordance with the invention the additives may be formed by using various molar ratios of reactants. Molar quantities (based on the dimercaptothiadiazole), less than molar quantities or more than molar quantities of a methacrylate or acrylate monomer, or of an amine can be used. The reaction conditions are conducted under conditions inert to the free radical reaction and at temperatures greater than ambient. By conditions inert to the free radical reaction is meant in the absence of oxygen and air. The elevated temperatures can range from above 30° up to about 180° C.

The additive reaction products can be used in lubricant compositions in amounts effective to impart to the lubricant oxidation stability and antiwear properties at extreme pressure. Such properties will be imparted to the lubricant by adding from about 0.01% to about 10% by weight, preferably from about 0.01 to about 3% of the neat product.

The lubricants which may be used with the additives (reaction products) of this invention are mineral and synthetic lubricating oils, mixtures thereof and greases made therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethyl-hexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof, (2) 2,2-disubstituted propane diols and (3) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5$–$C_9$ acids.

The following examples are offered to illustrate the invention. It is to be understood that the examples are merely illustrative and are not intended to limit the scope of the invention.

EXAMPLES

EXAMPLE 1

Dimercaotothiazdiazole-Butyl Methacrylate/Stearyl Methacrylate-Dodecylaniline Adduct In these examples, 2,5-dimercapto-1,3,4-thiadiazole (made by the reaction of hydrazine with carbon disulfide) was copolymerized with methacrylic alkyl esters and/or acrylic alkyl esters in the presence of radical initiators (catalyst) to form dimercaptothiadiazole-derived polymeric or oligomeric methacrylates and acrylates.

In this example, 30 grams of dimercaptothiadiazole (0.2 mole), 28.4 gm of butyl methacrylate (0.2 mol), 1.5 gm of azobisisobutyronitrile (AIBN, initiator), and 150 ml of methanol were mixed and brought to reflux temperature. During the heating process, the mixture became homogeneous at about 50° C. It was further stirred and refluxed for two hours, and then the volatiles were subsequently distilled under reduced pressure. The final reaction temperature was 100° C. Thereafter, dodecylaniline (26.1 gm, 0.1 mol) was added and the mixture was heated to 140° C. for two hours under reduced pressure. The resulting final product, a dark fluid, was completely soluble in n-hexane (weight: 141 gm).

EXAMPLE 2

Dimercaptothiadiazole-2-Ethylhexyl Acrylate-Dodecylaniline Adduct

To a 1-liter round-bottomed flask was charged 75 g of 2,5-dimercapto-1,3,4-thiadiazole (0.5 mol), 185.3 g of 2-ethylhexyl acrylate (1.0 mol), 300 ml of methanol, and 2.0 g of azobisisobutyronitrile. The mixture was stirred and heated to form a solution and then refluxed for 3 hrs. Methanol was then removed by vacuum distillation. The pot was cooled to about 70° C. and 65.3 g of dodecylaniline (0.25 mol) was added. The mixture was heated to 137° C. and held at this temperature for 2 hrs. under moderate vacuum. This produces 317.6 g of dark, viscous oil as desired product.

EXAMPLE 3

Dimercaptothiadiazide-2-Ethyhexyl Acrylate-Dodecylaniline Adduct

The procedure of Example 2 was followed with following exception: catalytic amount of 4-dimethylamino pyridine was used to assist the reaction of dodecylaniline with dimercaptothiadiazole-derived polymeric or oligomeric acrylates.

The dimercaptothiadiazole-derived polymeric or oligomeric methacrylates/acrylates, and their amine/amide, and ammonium salt derivatives were blended into mineral oils and evaluated for antiwear performance using the four-ball test (Method D-4172, TABLE 1).

TABLE 1

| Four-ball Wear Test (60 Kg, 2000 rpm, 30 min.) | | |
|---|---|---|
| | Wear Scar Diameter (mm) | |
| Item | 200° F. | 300° F. |
| Base oil (80% solvent refined bright oil, 20% solvent refined paraffinic neutral oil) | 3.49 | 4.24 |
| 1% of Example 1 in above base oil | 0.98 | 1.55 |
| 1% of Example 2 in above base oil | 1.00 | 1.47 |
| 1% of Example 3 in above base oil | 0.96 | — |

As can be seen from the above wear test results, the products exhibit considerable antiwear activity. The product of Example 1 as also blended into a fully formulated lubricating oil and evaluated for load carrying capability by FZG gear tester, and antioxidant activity by Mobil Method M334-2, Catalytic Oxidation Test at 325° F. for forty hours (TABLE 2).

TABLE 2

| | | Oxidation Test | |
|---|---|---|---|
| Item | FZG Test Fail Stage | Acid Number Increase | Percent Change In Viscosity |
| Base oil (fully formulated, solvent refined heavy bright oil) | <9 | >6 | >45 |
| 1% of Example 1 | 13 | 2.8 | 30 |

As shown above, the products of this invention show very good antiwear, extreme pressure properties as evidenced by improving wear characteristics and scoring load capacity from Stage 9 to Stage 13 in FZG tester. Also, the antioxidant activity is indicated by control of increase in acidity and viscosity.

The invention has been illustrated by specific embodiments in the examples. The invention is to be interpreted in accordance with the appended claims which are to be construed as including alternative equivalents and modifications within the skill of the art.

What is claimed is:

1. A product capable of imparting multifunctional antiwear/EP and antioxidation properties to a lubricant which is zinc and phosphorus free, comprising an adduct of a primary or secondary amine and a reaction product of a free radical reaction of components comprising (a) and (b), wherein
    (a) is 2,5-dimercapto-1,3,4-thiadiazole and
    (b) is $H_2C\!\!=\!\!C(R_1)C(O)OR_2$ or an oligomer thereof, wherein $R_1$ and $R_2$ are as defined below wherein the reaction product of said free radical reaction comprises a compound of the formula

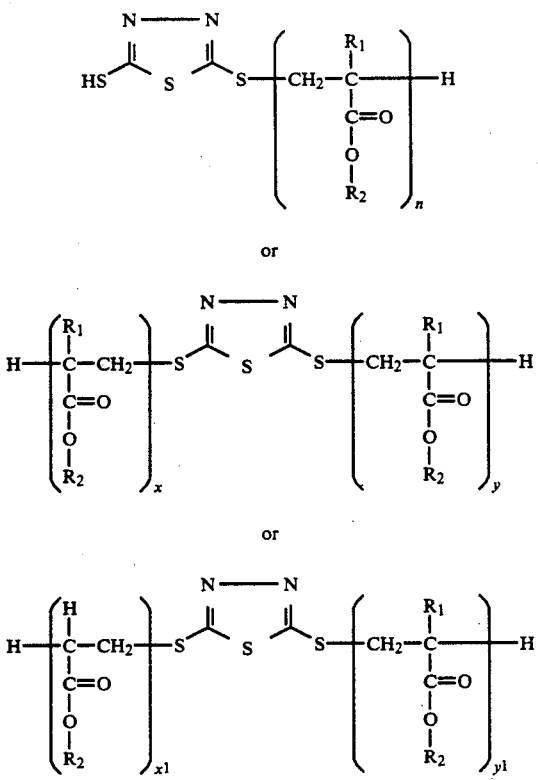

and wherein said adduct comprises at least one compound of the formula

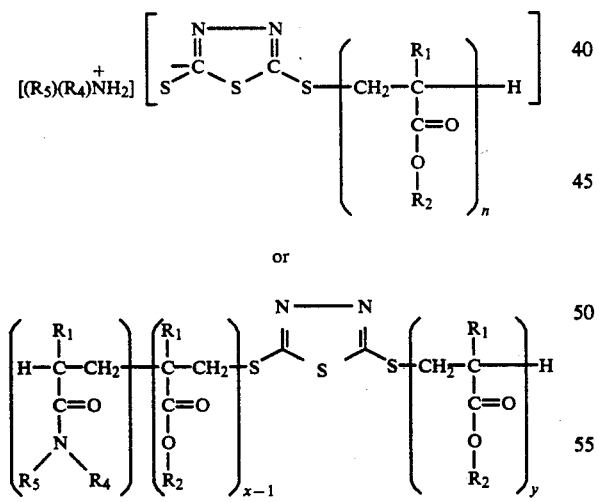

wherein $R_1$ is hydrogen or methyl,
wherein $R_2$ is hydrogen or a hydrocarbyl of 1 to 30 carbon atoms,
wherein N is nitrogen;
wherein x and y is a whole number, x is at least 1 and n is at least 1,
wherein each of $x^1$ and $y^1$ is 0 or a whole number but $x^1 + y^1$ is greater than 1,
wherein $R_4$ is hydrogen or a hydrocarbon group of 1 to 60 carbon atoms and $R_5$ is a hydrocarbon group of 1 to 60 carbon atoms wherein the hydrocarbon group is selected from the group consisting of alkyl, alkylene, cycloalkyl, aralkyl, aryl hydrocarboxyhydrocarbylene group, and a derivative of said alkyl, alkylene, aralkyl, aryl, and cycloalkyl containing an element selected from the group consisting of oxygen, sulfur and nitrogen.

2. The product of claim 1, wherein the primary of secondary amine contains 1 to 60 carbon atoms.

3. A lubricant composition comprising a major amount of an oil of lubricating viscosity or grease prepared therefrom and a minor amount of the adduct product of claim 2.

4. A lubricant composition comprising a major amount of an oil of lubricating viscosity or grease prepared therefrom and a minor amount of the adduct product of claim 1.

5. The composition of claim 4, wherein said oil of lubricating viscosity is selected from the group consisting of mineral, synthetic and mixtures of mineral and synthetic oils.

6. A zinc/phosphorus-free circulating oil or grease thereof comprising a major amount of said circulating oil or grease and a minor amount of a product of claim 1.

7. A process for producing an amine adduct of a dimercapto derivative of an acrylate, of an alkylacrylate or of a mixture of an alkyl acrylate and an acrylate, which comprises contacting 2,5-dimercapto-1,3,4-thiadiazole, in the presence of an amount of a radical initiator effective to cause the free radical polymerization of acrylates and alkylacrylates, with $M_1$, $M_2$ or a mixture of $M_1$ and $M_2$, wherein $M_1$ is the

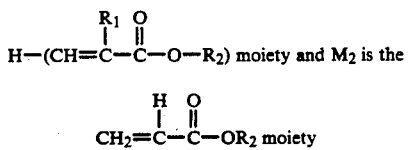

wherein $R_1$ is methyl and $R_2$ is hydrogen or an aliphatic group to 1 to 30 carbon atoms, to produce a product
wherein the product of said contacting is reacted with an amine having the formula $R_4R_5NH$ in which $R_4$ is hydrogen or a hydrocarbon group of 1 to 30 carbon atoms and $R_5$ is a hydrocarbon group of 1 to 30 carbon atoms.

8. The process of claim 7, wherein said contacting is undertaken in the absence of oxygen at a temperature above ambient.

* * * * *

UNITED STATES PATENT AND TRADEMARK OFFICE
CERTIFICATE OF CORRECTION

PATENT NO. : 5,188,746

DATED : February 23, 1993

INVENTOR(S) : Robert H. Davis et al.

It is certified that error appears in the above-identified patent and that said Letters Patent is hereby corrected as shown below:

On the title page, item (19) "Davis" should read --Davis et al--.

Item (75) inventors, should read:

-- Robert H. Davis
L. Oscar Farng
Gerassimos Frangatos
Andrew G. Horodysky--

Signed and Sealed this

Eleventh Day of January, 1994

Attest:

BRUCE LEHMAN

*Attesting Officer*  *Commissioner of Patents and Trademarks*